(12) United States Patent
Camp et al.

(10) Patent No.: US 11,453,673 B2
(45) Date of Patent: Sep. 27, 2022

(54) SUBSTITUTED [1,2,4]TRIAZOLO[4,3-A]PYRAZINES AS PHOSPHODIESTERASE INHIBITORS

(71) Applicant: Eli Lilly and Company, Indianapolis, IN (US)

(72) Inventors: Nicholas Paul Camp, Chertsey (GB); Chafiq Hamdouchi, Carmel, IN (US); Jayana Pankaj Lineswala, Brownsburg, IN (US); John Richard Morphy, Guildford (GB); Qing Shi, Carmel, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 165 days.

(21) Appl. No.: 16/956,826

(22) PCT Filed: Jan. 13, 2019

(86) PCT No.: PCT/US2019/015757
§ 371 (c)(1),
(2) Date: Jun. 22, 2020

(87) PCT Pub. No.: WO2019/156861
PCT Pub. Date: Aug. 15, 2019

(65) Prior Publication Data
US 2020/0399277 A1 Dec. 24, 2020

Related U.S. Application Data

(60) Provisional application No. 62/626,745, filed on Feb. 6, 2018.

(51) Int. Cl.
*A61K 31/4985* (2006.01)
*C07D 487/04* (2006.01)

(52) U.S. Cl.
CPC .................. *C07D 487/04* (2013.01)

(58) Field of Classification Search
CPC ................... A61K 31/4985; C07D 487/04
USPC .......................................... 514/249; 544/350
See application file for complete search history.

(56) References Cited

U.S. PATENT DOCUMENTS

| | | |
|---|---|---|
| 9,868,741 B2 | 1/2018 | Jesudason |
| 10,138,244 B2 | 11/2018 | Rekhter et al. |
| 2017/0233396 A1 | 8/2017 | Jesudason et al. |
| 2020/0123154 A1 | 4/2020 | Genin et al. |

FOREIGN PATENT DOCUMENTS

| WO | 2016/055618 A1 | 4/2016 |
|---|---|---|
| WO | 2017/139186 A1 | 8/2017 |

OTHER PUBLICATIONS

U.S. Appl. No. 16/628,164 Eli Lilly & Company, filed Jan. 2, 2020.
Dey et al., Selective Phosphodiesterase 1 Inhibitor BTTQ Reduces Blood Pressure in Spontaneously Hypertensive and Dahl Salt Sensitive Rats: Role of Peripheral Vasodilation, Frontiers in Physiology, 2020, vol. 11, Article 543727, pp. 1-10.
Wang et al., Generation and Phenotypic Characterization of Pde1a Mutant Mice, PLOS One, 2017, 12(7):e0181087, pp. 1-19.
Ye et al., Modulation of Polycystic Kidney Disease Severity by Phosphodiesterase 1 and 3 Subfamilies, Journal of the American Society of Nephrology, 2016, 27(5):1312-1320.

*Primary Examiner* — Douglas M Willis
(74) *Attorney, Agent, or Firm* — Quarles & Brady LLP

(57) ABSTRACT

The present invention provides a compound of Formula I: wherein $R^1$ is methyl, ethyl or cyclopropyl; $R^2$ is hydrogen, methyl, or ethyl; $R^3$ is methyl or AA; and $R^4$ is C2-C4 alkyl, BB; or a pharmaceutically acceptable salt thereof; for use as a PDE1 inhibitor.

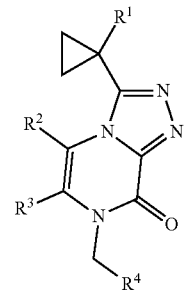

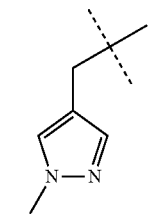

AA

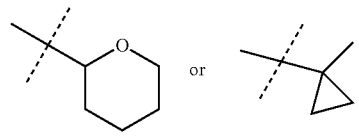

BB

12 Claims, No Drawings

SUBSTITUTED [1,2,4]TRIAZOLO[4,3-A]PYRAZINES AS PHOSPHODIESTERASE INHIBITORS

CROSS REFERENCE TO RELATED APPLICATIONS

This application is a 35 U.S.C. § 371 National Stage application of International Application Number PCT/US2019/015757 filed on Jan. 30, 2019, which claims priority to and benefit of U.S. Provisional Application No. 62/626,745 filed on Feb. 6, 2018, the contents of all of which are incorporated herein by reference in their entirety.

FIELD

The present invention relates to certain human PDE1 inhibitors, to pharmaceutical compositions comprising the compounds, to methods of using the compounds to treat physiological disorders, and to intermediates and processes useful in the synthesis of the compounds.

BACKGROUND

Phosphodiesterases (PDEs) are enzymes that regulate the cellular levels of cAMP and cGMP by controlling the rate at which these cyclic nucleotides are hydrolyzed. PDE1, a calcium and calmodulin-dependent PDE, is one of at least 11 known PDE families. PDE1 is expressed in many tissues, including the brain, heart, lung, kidney, and smooth muscle. The PDE1 is comprised of three known isoforms, PDE1A, PDE1B, and PDE1C.

Patients suffering from diabetes often develop a form of chronic kidney disease referred to as diabetic kidney disease (or diabetic nephropathy). It has been estimated that diabetic kidney disease may affect as many as 40 percent of diabetic patients. Treatment options for diabetic kidney disease are limited and include use of medications that lower blood pressure, management of blood glucose levels, diet, and weight, and implementation of regular physical activity. Thus, there is a need for additional treatment choices for patients suffering from chronic kidney disease, particularly diabetic kidney disease.

DETAILED DESCRIPTION

United States Patent Application Publication No. 2017/0233396 A1 discloses a certain [1,2,4]triazolo[4,3-a]quinoxalin-4-one and the use thereof in treating certain diseases, such as chronic kidney disease and diabetic kidney disease. WO 2016/055618 A1 discloses certain triazolopyrazinones as PDE1 inhibitors and their use for the treatment of neurodegenerative disorders and psychiatric disorders.

The present invention provides certain novel compounds that are inhibitors of human PDE1. The present invention provides certain novel compounds that are selective inhibitors of human PDE1A, PDE1B, and PDE1C relative to other human PDEs, such as PDE3A, PDE4D, and PDE6AB. Accordingly, the present invention provides a compound of Formula I.

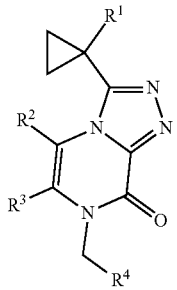

Formula I wherein $R^1$ is methyl, ethyl or cyclopropyl;
$R^2$ is hydrogen, methyl, or ethyl;
$R^3$ is methyl or

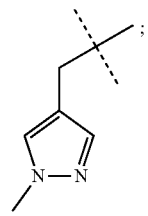

and
$R^4$ is C2-C4 alkyl,

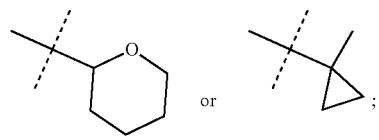

or a pharmaceutically acceptable salt thereof.

The present invention also provides a method of treating chronic kidney disease in a patient, comprising administering to a patient in need of such treatment an effective amount of a compound of Formula I. The present invention also provides a method of treating diabetic kidney disease in a patient, comprising administering to a patient in need of such treatment an effective amount of a compound of Formula I. The present invention also provides a method of treating hypertension in a patient, comprising administering to a patient in need of such treatment an effective amount of a compound of Formula I. The present invention also provides a method of treating heart failure in a patient, comprising administering to a patient in need of such treatment an effective amount of a compound of Formula I.

In addition, the invention provides a compound of Formula I for use in therapy. The invention further provides a compound of Formula I for use in for the treatment of chronic kidney disease. In addition, the invention provides a compound of Formula I for use in the treatment of diabetic kidney disease. In addition, the invention provides a compound of Formula I for use in the treatment of hypertension. The invention also provides a compound of Formula I for use in the treatment of heart failure. Furthermore, the invention provides the use of a compound of Formula I for the manufacture of a medicament for the treatment of chronic kidney disease. Furthermore, the invention provides the use of a compound of Formula I for the manufacture of a medicament for the treatment of diabetic kidney disease. The invention further provides the use of a compound of Formula I for the manufacture of a medicament for the treatment of hypertension. The invention also provides the use of a compound of Formula I for the manufacture of a medicament for the treatment of heart failure.

The invention further provides a pharmaceutical composition, comprising a compound of Formula I with one or more pharmaceutically acceptable carriers, diluents, or excipients. The invention further provides a process for preparing a pharmaceutical composition, comprising admixing a compound of Formula I with one or more pharmaceutically acceptable carriers, diluents, or excipients. This invention also encompasses novel intermediates and processes for the synthesis of compounds of Formula I.

As used herein, the terms "treating", "treatment", or "to treat" includes prohibiting, restraining, slowing, stopping, or reversing the progression or severity of an existing symptom or disorder.

As used herein, the term "patient" refers to a mammal, such as a dog or a human, with a human being preferred.

As used herein, the term "effective amount" refers to the amount or dose of compound of the invention, or a pharmaceutically acceptable salt thereof which, upon single or multiple dose administration to the patient, provides the desired effect in the patient under diagnosis or treatment.

As used herein the term "C2-C4 alkyl" refers to straight chain, branched, and cyclic alkyl groups selected from the group consisting of ethyl, n-propyl, isopropyl, cyclopropyl, n-butyl, sec-butyl, isobutyl, tert-butyl, and cyclobutyl, with ethyl, n-propyl, cyclopropyl, n-butyl, and cyclobutyl being preferred.

An effective amount can be readily determined by one skilled in the art using known techniques and by observing results obtained under analogous circumstances. In determining the effective amount for a patient, a number of factors are considered by one skilled in the art, including, but not limited to: the patient's size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

Compounds of the present invention are effective at a dosage per day that falls within the range of about 0.01 to about 20 mg/kg of body weight. In some instances dosage levels below the lower limit of the aforesaid range may be more than adequate, while in other cases still larger doses may be employed with acceptable side effects, and therefore the above dosage range is not intended to limit the scope of the invention in any way.

The compounds of the present invention are formulated as pharmaceutical compositions administered by any route which makes the compound bioavailable, including oral and parenteral routes. Most preferably, such compositions are for oral administration. Such pharmaceutical compositions and processes for preparing same are well known in the art (See, e.g., Remington: The Science and Practice of Pharmacy, L. V. Allen, Editor, 22$^{nd}$ Edition, Pharmaceutical Press, 2012).

The compounds of Formula I are particularly useful in the treatment methods of the invention, but certain groups, substituents, and compounds are preferred. The following paragraphs describe such preferred groups, substituents, and compounds. It will be understood that these preferences are applicable both to the treatment methods and to the new compounds of the invention.

It is preferred that $R^1$ is cyclopropyl.
It is preferred that $R^2$ is methyl.
It is preferred that $R^3$ is methyl.
It is further preferred that when $R^1$ is cyclopropyl, $R^2$ is methyl.
It is further preferred that when $R^2$ is methyl, $R^3$ is methyl.
It is more preferred that when $R^1$ is cyclopropyl, $R^2$ and $R^3$ are methyl.

The following compounds are especially preferred:

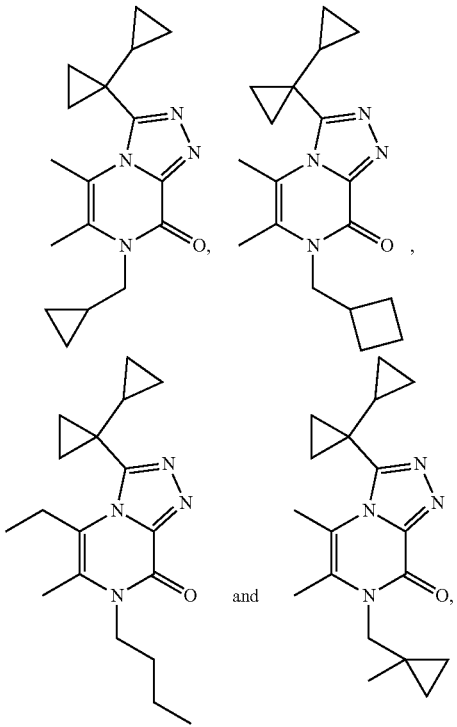

and the pharmaceutically acceptable salts thereof, with the corresponding free bases of each compound being most especially preferred.

A pharmaceutically acceptable salt of the compound of the invention may be formed, for example, by reaction of an appropriate free base of the compound of the invention and an appropriate pharmaceutically acceptable acid in a suitable solvent under standard conditions well known in the art. See, for example, Gould, P. L., "Salt selection for basic drugs," *International Journal of Pharmaceutics*, 33: 201-217 (1986); Bastin, R. J., et al. "Salt Selection and Optimization Procedures for Pharmaceutical New Chemical Entities," *Organic Process Research and Development*, 4: 427-435 (2000); and Berge, S. M., et al., "Pharmaceutical Salts," *Journal of Pharmaceutical Sciences*, 66: 1-19, (1977).

Individual isomers, enantiomers, and diastereomers may be separated or resolved by one of ordinary skill in the art at any convenient point in the synthesis of compounds of the invention, by methods such as selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994). The designations "isomer 1" and "isomer 2" refer to the compounds that elute from chiral chromatography under specified conditions, first and second, respectively.

Certain abbreviations are defined as follows: "ACN" refers to acetonitrile; "BSA" refers to Bovine Serum Albumin; "cAMP" refers to cyclic adenosine-3',5'-monophosphate; "CDI" refers to 1,1'-carbonyldiimidazole; "cGMP" refers to cyclic guanosine monophosphate; "DCC" refers to 1,3-dicyclohexylcarbodiimide; "DCM" refers to dichloromethane or methylene chloride; "DIC" refers to 1,3-diisopropylcarbodiimide; "DIPEA" refers to N,N-diisopropylethylamine; "DMF" refers to N,N-dimethylformamide; "DMAP" refers to dimethylaminopyridine; "DMSO" refers to dimethylsulfoxide; "EDCI" refers to 1-(3-dimethylaminopropyl)-3-ethylcarbodiimide hydrochloride; "EDTA" refers to ethylenediaminetetraacetic acid; "ES/MS" refers to Electrospray Mass Spectrometry; "EtOAc" refers to ethyl acetate; "Et$_2$O" refers to diethyl ether; "EtOH" refers to ethanol or ethyl alcohol; HATU" refers to 1-[bis(dimethylamino)methylene]-1H-1,2,3-triazolo[4,5-b]pyridinium 3-oxide hexafluorophosphate; "HBTU" refers to (1H-benzotriazol-1-yloxy)(dimethylamino)-N,N-dimethylmethanaminium hexafluorophosphate; "HIS" refers to histidine; "HOAt" refers to 1-hydroxy-7-azabenzotriazole; "HOBt" refers to 1-hydroxybenzotriazole hydrate; "IC$_{50}$" refers to the concentration of an agent that produces 50% of the maximal inhibitory response possible for that agent; "MeOH" refers to methanol or methyl alcohol; "MTBE" refers to methyl-tert-butyl ether; "NiNTA" refers to chromatography with an agarose stationary phase functionalized with nitrilotriacetic acid as chelator; "PDE" refers to phosphodiesterase; "PyBOP" refers to (benzotriazol-1-yloxytripyrrolidinophosphonium hexafluorophosphate); "PyBrOP" refers to bromo(tri-pyrrolidinyl)phosphoniumhexafluorophosphate; "t$_{(R)}$" refers to retention time; "SFC" refers to supercritical fluid chromatography; "SPA" refers to scintillation proximity assay; "TEA" refers to triethylamine; "THF" refers to tetrahydrofuran; "Tris" refers to 2-amino-2-hydroxymethyl-propane-1,3-diol; "U/mL" refers to units per milliliter; "XPhos Pd G2" refers to chloro(2-dicyclohexylphosphino-2',4',6'-triisopropyl-1,1'-biphenyl)[2-(2'-amino-1,1'-biphenyl)]palladium(II); and "ee" refers to enantiomeric excess.

The compounds of the present invention may be prepared by a variety of procedures known to one of ordinary skill in the art, some of which are illustrated in the schemes, preparations, and examples below. One of ordinary skill in the art recognizes that the specific synthetic steps for each of the routes described may be combined in different ways, or in conjunction with steps from different schemes, to prepare compounds of the invention. The products of each step below can be recovered by conventional methods well known in the art, including extraction, evaporation, precipitation, chromatography, filtration, trituration, and crystallization. In the schemes below, all substituents unless otherwise indicated, are as previously defined. The reagents and starting materials are readily available to one of ordinary skill in the art. Without limiting the scope of the invention, the following schemes, preparations, and examples are provided to further illustrate the invention.

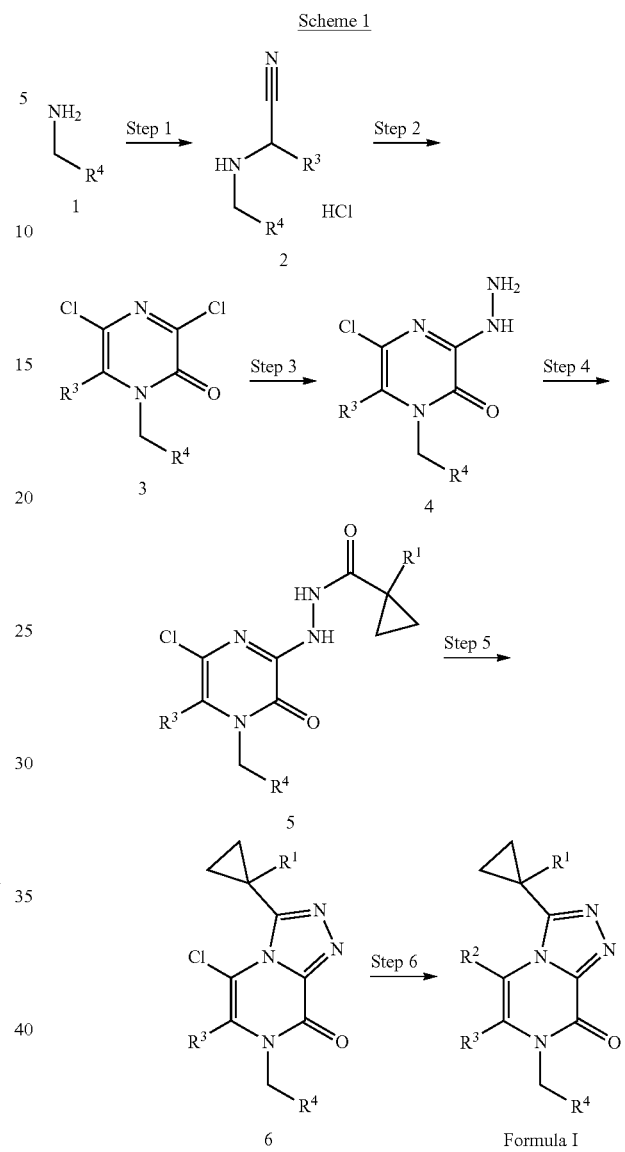

Scheme 1 depicts the alkylation of an amine (1) with a substituted nitrile to give compound (2) as shown in step 1. Trimethylsilyl cyanide can be used as a nitrile source with an aldehyde in a solvent such as 1,2-dimethoxyethane and heating to about 70° C. to accomplish the alkylation. The product can be treated with an acid such as HCl to isolate compound (2) as an acid salt. Alternatively, the alkylation can be completed using a hydroxy nitrile source and stirred in a solvent such as THF at room temperature and treated with an acid such as HCl to give compound (2). In step 2, compound (2) can be treated with an acid chloride, such as oxalyl chloride, dropwise at about 0° C. followed by heating the reaction to 50-100° C. to cyclize the nitrile to the 1,6-substituted-3,5-dichloro-pyrazin-2-one, compound (3). In step 3, compound (3) can then be converted to a hydrazide with hydrazine monohydrate in a solvent such as THF at room temperature or in EtOH with heating to about 100° C. to give the corresponding compound (4). In step 4, an amide coupling can be accomplished on compound (4) with the appropriate carboxylic acid, an organic base such as DIPEA in a solvent such as DMF or DCM and a coupling agent such as N-[(5-chloro-3-oxido-1H-benzotriazol-1-yl)-4-morpholinylmethylene]-N-methylmethanaminium hexafluorophosphate to give compound (5). One skilled in the art will recognize that there are a number of methods and reagents for amide formation resulting from the reaction of carboxylic acids and amines. For example, the reaction of the amine compound with an appropriate carboxylic acid in the presence of a coupling reagent with or without an organic base such as DIPEA or TEA can provide a compound of step 4. Coupling reagents include carbodiimides, such as DCC, DIC, EDCI or a carbonyldiimidazole such as CDI. Amide coupling additives, such as HOBt and HOAt can also be used to enhance the reaction. Additionally, uronium or phosphonium salts of non-nucleophilic anions, such as HBTU, HATU, PyBOP, and PyBrOP could be used in place of the more traditional coupling reagents. An additive such as DMAP may be used to enhance the reaction. Alternatively, compound (4) can be acylated using the appropriate acid chloride in the presence of a base, such as TEA or pyridine to give compound (5). In step 5, compound (5) can be cyclized under basic or acidic conditions to the triazole (6). For example, treatment of compound (5) with a base, such as TEA, and thionyl chloride in a solvent such as 1,4-dioxane and heating to about 80° C. in a closed system can provide triazole (6). Alternatively, hexamethyldisilazane can be used as a base and the reaction can be heated to about 120° C. After cooling to room temperature MeOH can be added to facilitate the cyclization. Alternatively, compound (5) can be cyclized to a triazole under acidic conditions using as acid such as acetic acid at a temperature of about 130° C. with microwave conditions to give triazole (6). In Step 6, two reactions can be accomplished. The 5-chloro substituent of compound (6) can be displaced resulting in the $R^2$ substituent of hydrogen and $R^3$ can be further functionalized under Suzuki palladium cross coupling conditions with a base such as potassium carbonate a suitable boronic reagent and a palladium catalyst such as bis (di-tert-butylphosphino)ferrocene palladium dichloride. The reaction can be heated in a solvent such as DMF at a temperature of about 120° C. to give compounds of Formula L The skilled artisan will recognize that there are a variety of conditions useful for facilitating such cross-coupling reactions. Suitable palladium reagents include XPhos Pd Gen 2, bis(triphenylphosphine)palladium(II) chloride, tris(dibenzylideneacetone)dipalladium (0) with tricyclohexylphosphine, (1,1'-bis(diphenylphosphino)ferrocene)palladium(II) chloride, palladium tetrakistriphenylphosphine, or palladium(II) acetate. Suitable bases include cesium carbonate, sodium carbonate, potassium carbonate, lithium tert-butoxide, or potassium phosphate tribasic monohydrate.

Scheme 2

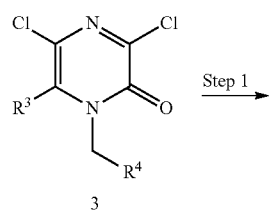

3

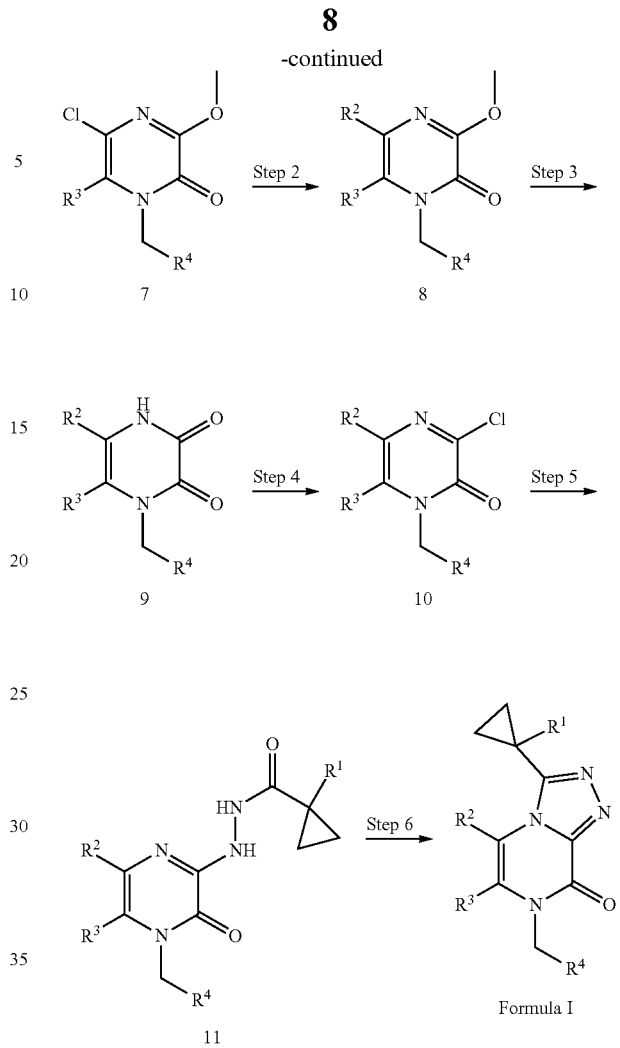

In Scheme 2, step 1, the 3-chloro substituent of compound (3) as prepared in Scheme 1, can be displaced with a methoxy using sodium methoxide at about 0° C. in a solvent such as MeOH to give compound (7). In step 2, the 5-chloro substituent of compound (7) can then be functionalized to substituents of $R^2$ in a Negishi palladium cross coupling reaction with a catalyst such as [1,3-bis(diphenylphosphino)propane]dichloronickel(II) and an appropriate organo zinc reagent in a solvent such as hexanes and with heating to about 80° C. to give compound (8). A person skilled in the art would be familiar with Negishi couplings that involve a transition metal catalyzed cross coupling. The reaction couples organic halides or triflates with organo zinc compounds forming carbon-carbon bonds. A palladium (0) species is commonly used as the metal catalyst but a nickel catalyst can also be utilized as described above. In step 3, a strong Lewis acid such as boron tribromide can be used to deprotect the hydroxy resulting in a 2,3-dione of compound (9). In step 4, the ketone in the 2-position can be selectively chlorinated using a chlorine source such as thionyl chloride and oxalyl chloride in a catalytic amount of DMF to give compound (10). In step 5, the chloro substituent on compound (10) can then be displaced with the appropriate carbohydrazide with heating to about 100° C. in a solvent such as THF to give compound (11). In step 6, compound (11) can then be cyclized as described in Scheme 1, Step 5 to give compounds of Formula I.

Scheme 3

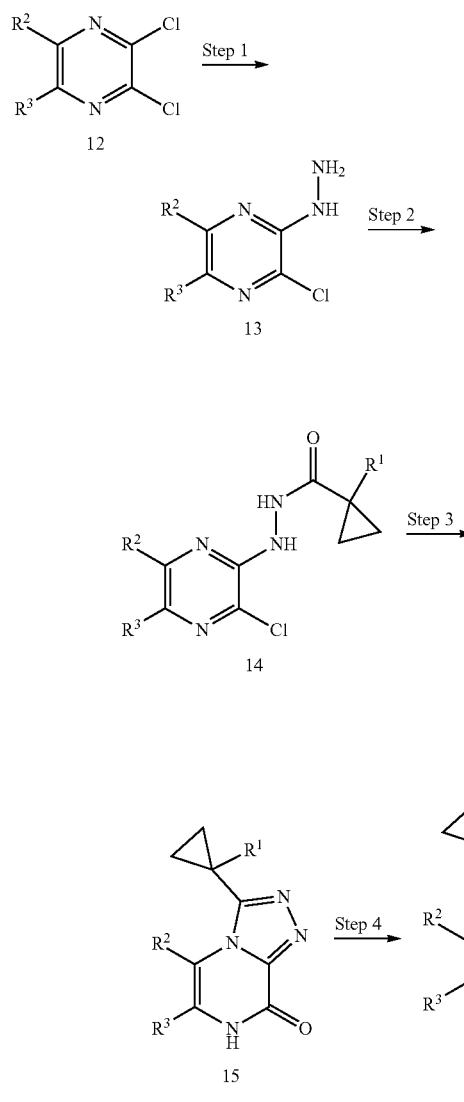

In Scheme 3, step 1, the 2-chloro substituent of a substituted 2,3-dichloro pyrazine (12) can be converted to compound (13) in a manner analogous to Scheme 1, step 3. In Scheme 3, step 2, compound (13) can be converted to compound (14) in a manner analogous to Scheme 1, step 4 with an amide coupling using a base such as DIPEA in a solvent such as DCM with a coupling agent such as HATU. In Scheme 3, step 3, the compound (14) can be cyclized in a manner analogous to Scheme 1, step 5 to give compound (15). In Scheme 3, step 4, the nitrogen of the pyrazine amide, compound (15), is alkylated with an $R^4$-halide using a strong non-nucleophilic base such as lithium bis(trimethylsilyl) amide in a solvent such as DMF and potassium iodide serving as a nucleophilic catalyst to give compounds of Formula I. Alternatively, other bases such as cesium carbonate or sodium hydride can be substituted for lithium bis(trimethylsilyl) amide and the mixture can be stirred at room temperature or heated at about 60-80° C. DMSO can serve as another solvent and the nucleophilic catalyst may not be needed for a successful reaction.

EXAMPLES

Preparation 1

2-(Cyclopropylmethylamino)propanenitrile hydrochloride

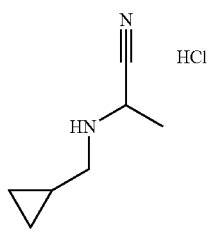

Scheme 1, step 1: Acetaldehyde (7.89 g, 179.1 mmol) is added slowly to a solution of cyclopropanemethylamine (10.00 g, 137.7 mmol) in 1,2-dimethoxyethane (78.40 mL, 756.4 mmol) at 0° C. and stirred at room temperature for 30 minutes followed by the dropwise addition of trimethylsilyl cyanide (20.29 mL, 151.5 mmol). The resulting reaction mixture is heated at 70° C. for 4 hours, and cooled at room temperature. The reaction is cooled to 0° C. and HCl (37.893 mL, 151.570 mmol) is added dropwise under a $N_2$ atmosphere. The resulting precipitate is filtered and washed with ether (200 mL) to give the title compound (22.31 g, 97%). $^1$H NMR (400 MHz, CDCl$_3$) δ 11.08-11.04 (bs, 1H), 4.42 (q, J=7.0 Hz, 1H), 3.19 (dd, J=7.1, 13.0 Hz, 1H), 2.97 (dd, J=7.8, 12.7 Hz, 1H), 1.95 (d, J=7.3 Hz, 3H), 1.37-1.29 (m, 1H), 0.81-0.73 (m, 2H), 0.58-0.52 (m, 2H).

Preparation 2

2-(Butylamino)propanenitrile;hydrochloride

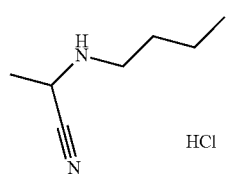

Scheme 1, step 1: A solution of butylamine (6.77 mL, 68.4 mmol) and 2-hydroxypropanenitrile (7.39 mL, 103 mmol) in THF (68.4 mL) is stirred at room temperature overnight. The reaction mixture is concentrated under reduced pressure, diluted with Et$_2$O and HCl (68 mL, 1.0 mol/L in Et$_2$O) is added drop wise. The solid formed is collected by filtration to give the title compound (9.67 g, 86.9%). $^1$H NMR (400 MHz, d$_6$-DMSO) δ 9.96 (br s, 2H), 4.62 (br s, 1H), 2.96 (t, J=8 Hz, 2H), 1.64-1.56 (m, 5H), 1.39-1.30 (m, 2H), 0.885 (t, J=7.2 Hz, 3H).

Preparation 3

1-Cyclopropylcyclopropanecarbohydrazide hydrochloride

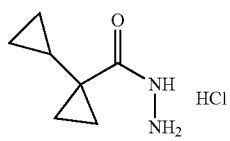

To a stirred solution of 1-cyclopropylcyclopropanecarboxylic acid (9.63 g, 76.3 mmol), and HATU (32.3 g, 83.2 mmol) in DMF (300 mL) is added tert-butyl carbazate (5.00 g, 37.8 mmol) followed by DIPEA (14.5 mL, 83.1 mmol), and the reaction is stirred at room temperature for 5 days. The reaction mixture is diluted with EtOAc, washed with 1.0 N HCl, saturated NaHCO$_3$, and water. The organic layer is isolated, dried over magnesium sulfate, filtered, and concentrated under reduced pressure. 1,4-Dioxane (50 mL) is added to the residue, HCl (4 mol/L) in 1,4-dioxane (100 mL, 400 mmol) is added over 20 minutes and the reaction is stirred at room temperature for 1 hour. The solution is filtered, the filter cake is washed with MTBE, and dried under reduced pressure to give the title compound (8.01 g, 58.7%). MS (m/z) 141 (M+H).

Preparation 4

(1-Methylcyclopropyl)methyl methanesulfonate

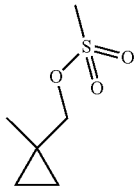

A stirred solution of (1-methylcyclopropyl)methanol (500 mg, 5.805 mmol) and TEA (0.89 mL, 6.39 mmol) in DCM (30 mL) is cooled to 0° C. in an ice/water bath. Methanesulfonyl chloride (0.5 mL, 6.46 mmol) is added drop wise via a syringe. The reaction mixture is allowed to warm to room temperature; then stirred for 1 hour. The reaction is diluted with saturated NaHCO$_3$ and extracted with DCM. The organics are dried over anhydrous sodium sulfate, filtered, and concentrated under reduced pressure to give the title compound (1.00 g, 94%). $^1$H NMR (400 MHz, d$_6$-DMSO) δ 3.97 (s, 2H), 3.11 (s, 3H), 1.09 (s, 3H), 0.534-0.509 (m, 2H), 0.404-0.378 (m, 2H).

Preparation 5

3,5-Dichloro-1-(cyclopropylmethyl)-6-methyl-pyrazin-2-one

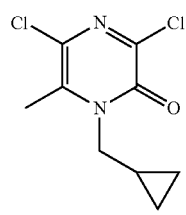

Scheme 1, step 2: A solution of 2-(cyclopropylmethylamino)propanenitrile;hydrochloride (22.31 g, 134.71 mmol) in 1,2-dimethoxyethane (216.41 mL; 2.09 moles) is cooled to 0° C. and oxalyl chloride (23.37 mL, 269.42 mmol) is added dropwise under a N$_2$ atmosphere. The reaction mixture is then allowed to reach room temperature, and heated at 100° C. for 6 hours. The reaction is cooled to room temperature and stirred overnight. The excess oxalyl chloride is removed under reduced pressure. The mixture is neutralized with saturated bicarbonate solution (100 mL) and extracted with EtOAc (3×350 ml). The organic extracts are combined and washed with brine, dried over sodium sulfate, filtered, and concentrated under reduced pressure to give crude material. The residue is purified by silica gel flash chromatography, eluting with EtOAc:hexanes to give the title compound (21.33 g, 67.93%). MS (m/z) 235 (M+H).

Preparation 6

1-Butyl-3,5-dichloro-6-methyl-pyrazin-2-one

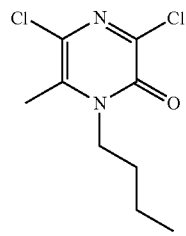

Scheme 1, step 2: A stirred suspension of 2-(butylamino)propanenitrile hydrochloride (9.67 g, 59.4 mmol) in toluene (300 mL) is cooled to 0° C. in an ice/water bath. Oxalyl chloride (26.0 mL, 299.7 mmol) is added drop wise. The reaction is stirred at 55° C. for 16 hours, cooled to room temperature, and concentrated under reduced pressure. The residue is purified by flash chromatography on silica, eluting with 0-20% EtOAc in hexanes to give the title compound (14.93 g, >99%). MS (m/z) 235 (M+H).

Preparation 7

1-Butyl-5-chloro-3-methoxy-6-methyl-pyrazin-2-one

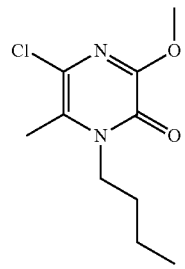

Scheme 2, step 1: A stirred solution of 1-butyl-3,5-dichloro-6-methyl-pyrazin-2-one (12.61 g, 50.42 mmol) in MeOH (15 mL) is cooled to 0° C. in an ice/water bath. Sodium methoxide (15 mL, 67 mmol, 25 mass % in MeOH) is added and the mixture is stirred for 20 minutes. The reaction is diluted with water, the solids are collected by filtration, and dried under reduced pressure to give the title compound (9.39 g, 80.8%). MS (m/z) 231 (M+H).

Preparation 8

1-Butyl-5-ethyl-3-methoxy-6-methyl-pyrazin-2-one

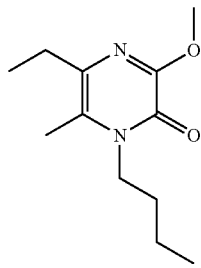 [SMILES: CCCCn1c(C)c(CC)nc(OC)c1=O]

Scheme 2, step 2: 1-Butyl-5-chloro-3-methoxy-6-methyl-pyrazin-2-one (500 mg, 2.16 mmol) and [1,3-bis(diphenylphosphino)propane]dichloronickel(II) (120 mg, 0.221 mmol) are combined in a vial. The vial is sealed under N, THF (5.5 mL) and a solution of diethylzinc (6.5 mL, 6.5 mmol, 1 mol/L in hexanes) are added, and the reaction is stirred at 80° C. overnight. The reaction is cooled to room temperature, combined with material prepared essentially by the same method (50 mg scale reaction), and filtered over diatomaceous earth. The diatomaceous earth is washed with MTBE and water, and filtrate is collected. The aqueous material is extracted with MTBE (2×), the combined organics are washed with brine, dried over anhydrous sodium sulfate, filtered, and concentrated under reduced pressure. The residue is purified by flash chromatography on silica, eluting with 0-70% EtOAc in hexanes to give the title compound (343.1 mg, 64%, combined yield). MS (m/z) 225 (M+H).

Preparation 9

4-Butyl-6-ethyl-5-methyl-1H-pyrazine-2,3-dione

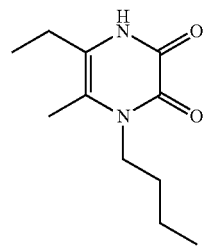

Scheme 2, step 3: A stirred solution of 1-butyl-5-ethyl-3-methoxy-6-methyl-pyrazin-2-one (343.1 mg, 1.53 mmol) in DCM (10 mL) is cooled to 0° C. in an ice/water bath. Boron tribromide (3 mL, 3 mmol, 1 mol/L in DCM) is added, the reaction is stirred for 2 hours, and then it is warmed to room temperature and stirred for 45 minutes. The reaction is quenched with saturated NaHCO$_3$, and the aqueous is extracted with DCM (3×). The combined organic extracts are washed with brine, dried over anhydrous sodium sulfate, filtered, and concentrated under reduced pressure to give the title compound (320.3 mg, 89%). MS (m/z) 211 (M+H).

Preparation 10

1-Butyl-3-chloro-5-ethyl-6-methyl-pyrazin-2-one

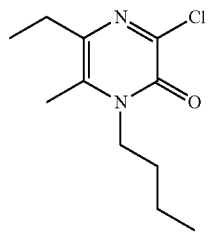

Scheme 2, step 4: A solution of 4-butyl-6-ethyl-5-methyl-1H-pyrazine-2,3-dione (301.3 mg, 1.29 mmol), thionyl chloride (1.0 mL, 13.73 mmol) and catalytic DMF (3 drops) in DCM (6 mL) is stirred at room temperature for 45 minutes. Additional thionyl chloride (1.0 mL, 13.73 mmol) is added and the reaction is stirred for an additional 45 minutes. The reaction is concentrated under reduced pressure. The residue is suspended in toluene and concentrated under reduced pressure (2×) to give the title compound (475.9 mg, 96.8%, 60 mass %). MS (m/z) 229 (M+H).

Preparation 11

5-Chloro-1-(cyclopropylmethyl)-3-hydrazino-6-methyl-pyrazin-2-one

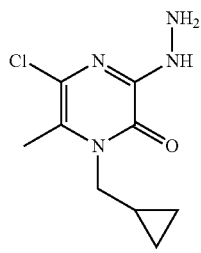

Scheme 1, step 3: Hydrazine monohydrate (15.3 mL, 201.3 mmol) is added dropwise to a solution of 3,5-dichloro-1-(cyclopropylmethyl)-6-methyl-pyrazin-2-one (21.33 g, 91.51 mmol) in THF (106.7 mL, 1311 mmol), cooled to 0° C., stirred for 15 minutes, then at room temperature for 16 hours. Water (100 mL) is added and the mixture is extracted with DCM (300 mL). The organic extract is concentrated under reduced pressure to give a yellow solid which is triturated in Et$_2$O (100 mL) and then filtered to give the title compound (0.26 g, 82%). MS (m/z) 229 (M+H).

Preparation 12

N'-[6-Chloro-4-(cyclopropylmethyl)-5-methyl-3-oxo-pyrazin-2-yl]-1-cyclopropyl-cyclopropanecarbohydrazide

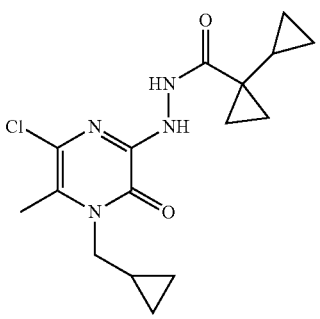 [SMILES: Cc1c(Cl)nc(NNC(=O)C2(C3CC3)CC2)c(=O)n1CC1CC1]

Scheme 1, step 4: 1-Cyclopropylcyclopropanecarboxylic acid (10.13 g, 80.28 mmol) is added to a stirred solution of 5-chloro-1-(cyclopropylmethyl)-3-hydrazino-6-methyl-pyrazin-2-one (16.69 g, 72.98 mmol) and DIPEA (42.00 mL, 240.8 mmol) in dry DMF (417.3 mL) under a N$_2$ atmosphere at room temperature followed by the addition of N-[(5-chloro-3-oxido-1H-benzotriazol-1-yl)-4-morpholinylmethylene]-N-methylmethanaminium hexafluorophosphate (36.59 g, 80.28 mmol). The reaction mixture is stirred at room temperature for 2 hours. Water (1.4 L) is added to the reaction mixture and a precipitate forms. The reaction mixture is filtered and the isolated solid is washed with Et$_2$O (1 L) to give the title compound (16.06 g, 65%). MS (m/z) 339 (M+H).

Preparation 13

N'-(4-Butyl-6-ethyl-5-methyl-3-oxo-pyrazin-2-yl)-1-cyclopropyl-cyclopropanecarbohydrazide Scheme 2, step 5: 1-Butyl-3-chloro-5-ethyl-6-methyl-pyrazin-2-one (475.9 mg, 1.25 mmol, 60 mass %), 1-cyclopropylcyclopropanecarbohydrazide;hydrochloride (221 mg, 1.25 mmol), and THF (4 mL) are combined in a microwave vial sealed under N$_2$ and stirred at 100° C. for 2 hours under microwave conditions. The reaction is diluted with water and is extracted with DCM (3×). The combined organic extracts are washed with brine, dried over anhydrous sodium sulfate, filtered, and concentrated under reduced pressure to give the title compound (320.3 mg, 89%, 70 mass %). MS (m/z) 333 (M+H).

Preparation 14

(3-Chloro-5,6-dimethyl-pyrazin-2-yl)hydrazine

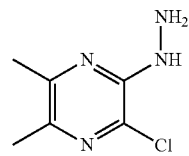

Scheme 3, step 1: A stirred solution of 2,3-dichloro-5,6-dimethyl-pyrazine (2.0 g, 11.298 mmol) and hydrazine (0.943 mL, 28.2 mmol, 95 mass %) in EtOH (15 mL) is heated at 100° C. overnight. The reaction mixture is concentrated under reduced pressure to give the title compound (1.94 g, 84.6%). MS (m/z) 173 (M+H).

Preparation 15

N'-(3-Chloro-5,6-dimethyl-pyrazin-2-yl)-1-cyclopropyl-cyclopropanecarbohydrazide

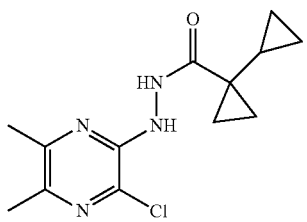 [SMILES: Cc1nc(Cl)c(NNC(=O)C2(C3CC3)CC2)nc1C]

Scheme 3, step 2: (3-Chloro-5,6-dimethyl-pyrazin-2-yl)hydrazine (4.08 g, 23.6 mmol), 1-cyclopropylcyclopropanecarboxylic acid (4.77 g, 37.8 mmol), HATU (14.7 g, 37.9 mmol) and DIPEA (14.4 mL, 82.6 mmol) are dissolved in DCM (120 ml) and stirred at room temperature for 45 minutes. The reaction mixture is washed with water, dried over sodium sulfate and concentrated under reduced pressure. The residue is purified by flash chromatography on silica, eluting with 0-100% EtOAc in hexanes to give the title compound (4.37 g, 65.8%). MS (m/z) 280 (M+H).

The following compounds are prepared in a manner essentially analogous to the method of Preparation 15.

TABLE 1

| Prep. No. | Chemical name | Structure | MS (m/z) (M + H) |
|---|---|---|---|
| 16 | N'-(3-Chloro-5,6-dimethyl-pyrazin-2-yl)-1-ethyl-cyclopropanecarbohydrazide | 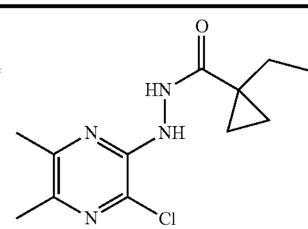 | 269 |
| 17 | N'-(3-Chloro-5,6-dimethyl-pyrazin-2-yl)-1-methyl-cyclopropanecarbohydrazide | 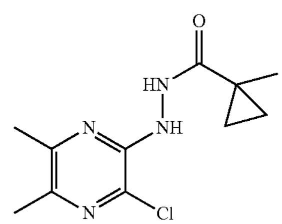 | 255 |

Preparation 18

5-Chloro-3-(1-cyclopropylcyclopropyl)-7-(cyclopropylmethyl)-6-methyl-[1,2,4]triazolo[4,3-a]pyrazin-8-one

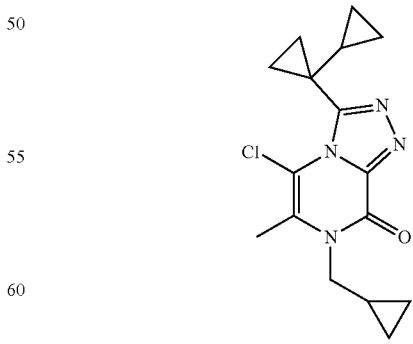

Scheme 1, step 5: N'-[6-Chloro-4-(cyclopropylmethyl)-5-methyl-3-oxo-pyrazin-2-yl]-1-cyclopropyl-cyclopropanecarbohydrazide (18.44 g, 54.75 mmoles) is added to 1,4-dioxane (547.5 mL, 6413 mmol) followed by the addition of TEA (30.52 mL, 219.0 mmol) and thionyl chloride (7.98 mL, 109.5 mmoles). The reactor is closed and stirred at room temperature for 30 minutes and then heated at 80° C. for two hours. The reaction is cooled to room temperature and water (1 L) is added. The mixture is extracted with DCM (2×750 ml). The organic extracts are combined and dried over sodium sulfate; filtered, and concentrated under reduced pressure to give a residue. The residue is purified by silica gel flash chromatography, eluting with EtOAc:hexanes to give the title compound (9.2 g, 52%). MS (m/z) 321 (M+H).

Preparation 19

3-(1-Cyclopropylcyclopropyl)-5,6-dimethyl-7H-[1,2,4]triazolo[4,3-a]pyrazin-8-one

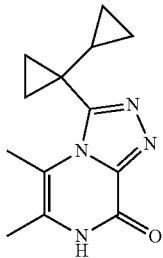 [SMILES: Cc1[nH]c(=O)c2nnc(C3(C4CC4)CC3)n2c1C]

Scheme 3, step 3: N'-(3-Chloro-5,6-dimethyl-pyrazin-2-yl)-1-cyclopropyl-cyclopropanecarbohydrazide (3.74 g, 7.99 mmol, 60 mass %) is dissolved in acetic acid (15 mL), and heated under microwave irradiation for 3 hours at 130° C. The reaction is cooled to room temperature, the solids are collected by filtration and washed with hexanes to give the title compound (1.98 g, 100%). MS (m/z) 245 (M+H). The following compounds are prepared in a manner essentially analogous to the method of Preparation 19.

TABLE 2

| Prep. No. | Chemical name | Structure | MS (m/z) (M + H) |
|---|---|---|---|
| 20 | 5,6-Dimethyl-3-(1-methylcyclopropyl)-7H-[1,2,4]triazolo[4,3-a]pyrazin-8-one | 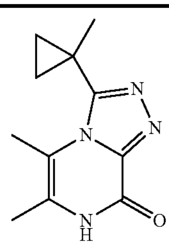 | 219 |
| 21 | 3-(1-Ethylcyclopropyl)-5,6-dimethyl-7H-[1,2,4]triazolo[4,3-a]pyrazin-8-one | 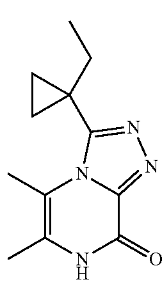 [SMILES: CCC1(c2nnc3c(=O)[nH]c(C)c(C)n23)CC1] | 233 |

Example 1

3-(1-Cyclopropylcyclopropyl)-7-(cyclopropylmethyl)-6-[(1-methylpyrazol-4-yl)methyl]-[1,2,4]triazolo[4,3-a]pyrazin-8-one

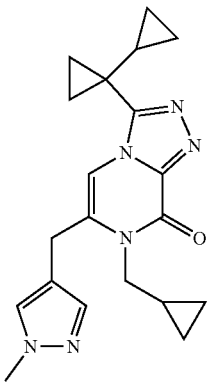 [SMILES: Cn1cc(Cc2cn3c(C4(C5CC5)CC4)nnc3c(=O)n2CC2CC2)cn1]

Scheme 1, step 6: Potassium carbonate (0.127 g, 0.922 mmol) is added to the solution of 5-chloro-3-(1-cyclopropylcyclopropyl)-7-(cyclopropylmethyl)-6-methyl-[1,2,4]triazolo[4,3-a]pyrazin-8-one (0.098 g, 0.307 mmol) and 1-methyl-4-(4,4,5,5-tetramethyl-1,3,2-dioxaborolan-2-yl)pyrazole (0.0476 g, 0.229 mmol) in DMF (4.0 mL). The reaction is degassed and purged with $N_2$ for 10 minutes. 1,1'-Bis (di-tert-butylphosphino)ferrocene palladium dichloride (0.015 g, 0.022 mmol) is added to the reaction and the mixture is heated at 120° C. for 16 hours. The reaction is partitioned between EtOAc and cold saturated solution of $NaHCO_3$, and separated. The organic layer is washed with 5% lithium chloride (aqueous), followed by brine, dried over anhydrous sodium sulfate, filtered, and concentrated under reduced pressure. The residue is purified by silica gel flash chromatography eluting with 0-100% acetone in hexanes to give the title compound (0.015 mg, 13%). MS (m/z) 365 (M+H).

Example 2

3-(1-Cyclopropylcyclopropyl)-7-(cyclopropylmethyl)-5,6-dimethyl-[1,2,4]triazolo[4,3-a]pyrazin-8-one

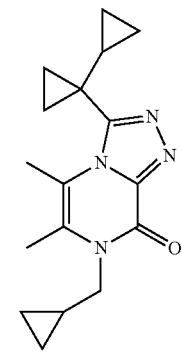 [SMILES: Cc1c(C)n2c(C3(C4CC4)CC3)nnc2c(=O)n1CC1CC1]

Scheme 3, step 4: Lithium bis(trimethylsilyl)amide (2.5 mL, 2.5 mmol, 1 mol/L in MTBE) is added to 3-(1- cyclopropylcyclopropyl)-5,6-dimethyl-7H-[1,2,4]triazolo[4,3-a]pyrazin-8-one (202 mg, 0.827 mmol) in DMF (8 mL) and the reaction is stirred at room temperature for 1 hour. (Bromomethyl)cyclopropane (400 μL, 4 mmol) and potassium iodide (15 mg, 0.0909 mmol) are added and the reaction is stirred at room temperature overnight. Additional (bromomethyl)cyclopropane (80 μL, 0.8 mmol) and potassium iodide (15 mg, 0.0909 mmol) are added, the reaction is stirred at room temperature for 4 hours and then is stirred at 35° C. overnight. The reaction is partitioned between EtOAc and water, and separated. The aqueous material is extracted with EtOAc. The organic layers are washed with 5% lithium chloride (aqueous), followed by brine, dried over anhydrous sodium sulfate, filtered, and concentrated under reduced pressure. The residue is combined with previous materials prepared essentially the same manner as described in Alternate Example 2 and purified by silica gel flash chromatography eluting with 0-10% MeOH in DCM. The isolated material is combined with previous material prepared in essentially the same manner (51 mg scale reaction) and recrystallized from EtOAc and dried in a vacuum oven to give the title compound (140.3 mg, 16% combined yield). MS (m/z) 299 (M+H).

The following compounds are prepared in a manner essentially analogous to the method of Example 2

TABLE 3

| Ex. No. | Chemical name | Structure | MS (m/z) (M + H) |
|---|---|---|---|
| 3 | 3-(1-Cyclopropylcyclopropyl)-5,6-dimethyl-7-pentyl-[1,2,4]triazolo[4,3-a]pyrazin-8-one | 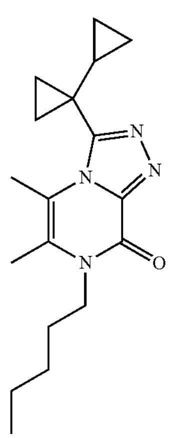 [SMILES: CCCCCn1c(C)c(C)n2c(C3(C4CC4)CC3)nnc2c1=O] | 315 |
| 4 | 7-(Cyclobutylmethyl)-3-(1-cyclopropylcyclopropyl)-5,6-dimethyl-[1,2,4]triazolo[4,3-a]pyrazin-8-one | 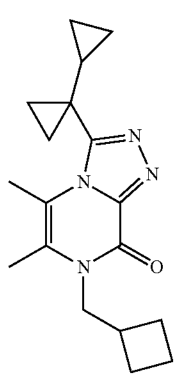 [SMILES: Cc1c(C)n2c(C3(C4CC4)CC3)nnc2c(=O)n1CC1CCC1] | 313 |

Alternate Example 2

3-(1-Cyclopropylcyclopropyl)-7-(cyclopropylmethyl)-5,6-dimethyl-[1,2,4]triazolo[4,3-a]pyrazin-8-one Scheme 3, step 4: 5,6-Dimethyl-3-(1-methylcyclopropyl)-7H-[1,2,4]triazolo[4,3-a]pyrazin-8-one (25 mg, 0.07 mmol), cesium carbonate (100 mg, 0.31 mmol), potassium iodide (3 mg, 0.02 mmol) and bromomethylcyclopropane (25 μL, 0.26 mmol) are combined in DMF (1 mL). The mixture is stirred under $N_2$ at 80° C. overnight. The reaction is cooled to room temperature and is diluted with EtOAc and washed with water (2×). The organic layer is washed with 5% lithium chloride (aqueous), dried over anhydrous sodium sulfate, separated, and concentrated under reduced pressure. The residue is purified by silica gel flash chromatography eluting with 0-15% MeOH in DCM to give the title compound (8 mg, 3.7%). MS (m/z) 299 (M+H).

Example 5

7-Butyl-3-(1-cyclopropylcyclopropyl)-5,6-dimethyl-[1,2,4]triazolo[4,3-a]pyrazin-8-one

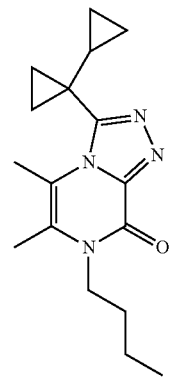 [SMILES: CCCCn1c(C)c(C)n2c(C3(C4CC4)CC3)nnc2c1=O]

Scheme 3, step 4: Sodium hydride (950 mg, 23.75 mmol, 60 mass % in mineral oil) is added to 3-(1-cyclopropylcyclopropyl)-5,6-dimethyl-7H-[1,2,4]triazolo[4,3-a]pyrazin-8-one (1.95 g, 7.98 mmol) in DMF (50 mL) at 0° C. 1-Bromobutane (2.15 mL, 19.9 mmol) is added and the reaction is stirred at room temperature overnight. The reaction is then stirred at 60° C. for 2 hours. The reaction is cooled to room temperature and diluted with EtOAc. The organic layer is washed with brine, dried over anhydrous sodium sulfate, filtered, and concentrated under reduced pressure. The residue is purified by flash chromatography on silica, eluting with 0-50% EtOAc in hexanes and then 0-10% MeOH in DCM. Chromatography fractions containing product are combined, concentrated under reduced pressure. The impure residue is purified by flash chromatography on silica, eluting in 0-100% EtOAc in DCM. Chromatography fractions containing product are combined, concentrated under reduced pressure and lyophilized to give the title compound (100 mg, 4.7%) MS (m/z) 301 (M+H).

Example 6

Racemic 3-(1-cyclopropylcyclopropyl)-5,6-dimethyl-7-(tetrahydropyran-2-ylmethyl)-[1,2,4]triazolo[4,3-a]pyrazin-8-one

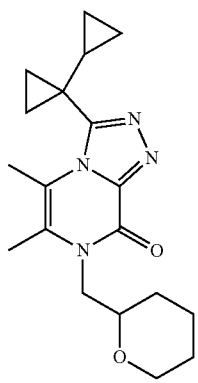 [SMILES: Cc1c(C)n2c(C3(C4CC4)CC3)nnc2c(=O)n1CC1CCCCO1]

Scheme 3, step 4: 3-(1-Cyclopropylcyclopropyl)-5,6-dimethyl-7H-[1,2,4]triazolo[4,3-a]pyrazin-8-one (1.95 g, 7.98 mmol), cesium carbonate (7.75 g, 23.8 mmol), potassium iodide (131 mg, 0.789 mmol) and 2-(bromomethyl)tetrahydro-2H-pyran (1.80 mL, 17.8 mmol) are combined in DMF (66 mL). The mixture is stirred under $N_2$ at 80° C. for 6 hours. The reaction is cooled to room temperature and is diluted with 3:1 chloroform/isopropanol. The organics are washed with saturated $NaHCO_3$, followed by brine, dried over anhydrous sodium sulfate, filtered, and concentrated under reduced pressure. The residue is purified by silica gel flash chromatography on silica, eluting with 0-100% EtOAc in hexanes and then 0-10% MeOH in DCM to give the title compound (275 mg, 10%). MS (m/z) 343 (M+H).

The following compounds are prepared in a manner essentially analogous to the method of Example 6.

TABLE 4

| Ex. No. | Chemical name | Structure | MS (m/z) (M + H) |
|---|---|---|---|
| 7 | Racemic 3-(1-Ethylcyclopropyl)-5,6-dimethyl-7-(tetrahydropyran-2-ylmethyl)-[1,2,4]triazolo[4,3-a]pyrazin-8-one | 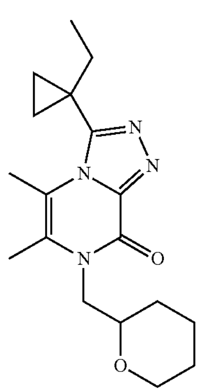 [SMILES: CCC1(c2nnc3c(=O)n(CC4CCCCO4)c(C)c(C)n23)CC1] | 331 |
| 8 | Racemic 5,6-Dimethyl-3-(1-methylcyclopropyl)-7-(tetrahydropyran-2-ylmethyl)-[1,2,4]triazolo[4,3-a]pyrazin-8-one | | 317 |

Example 9

3-(1-Cyclopropylcyclopropyl)-5,6-dimethyl-7-(tetrahydropyran-2-ylmethyl)-[1,2,4]triazolo[4,3-a]pyrazin-8-one; Isomer 1 and

Example 10

3-(1-Cyclopropylcyclopropyl)-5,6-dimethyl-7-(tetrahydropyran-2-yl]methyl]-[1,2,4]triazolo[4,3-a]pyrazin-8-one; Isomer 2

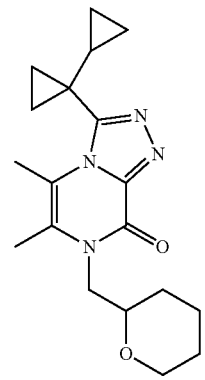 [SMILES: Cc1c(C)n2c(C3(C4CC4)CC3)nnc2c(=O)n1CC1CCCCO1]

Racemic 3-(1-cyclopropylcyclopropyl)-5,6-dimethyl-7-(tetrahydropyran-2-yl]methyl]-[1,2,4]triazolo[4,3-a]pyrazin-8-one (250 mg, 0.730 mmol) is separated into its constituent enantiomers by chiral chromatography with the following conditions: Column (S,S) Whelk-01 25 cm×21.2 mm, 10μ, 21×250 mm, mobile phase 35% MeOH: 65% $CO_2$, column temperature 40° C., flow rate 5 mL/minute, UV 225. The first eluting material is lyophilized to give the title compound of Example 9 (95 mg, 38%), MS (m/z) 343 (M+H), $t_{(R)}$=1.81 minutes, ee >99%. The second eluting isomer is lyophilized to give the title compound of Example 10 (95 mg, 38%), MS (m/z) 343 (M+H), $t_{(R)}$=2.62 minutes, ee >99%.

Example 11

3-(1-Ethylcyclopropyl)-5,6-dimethyl-7-(tetrahydropyran-2-ylmethyl)-[1,2,4]triazolo[4,3-a]pyrazin-8-one, Isomer 1 and

Example 12

3-(1-Ethylcyclopropyl)-5,6-dimethyl-7-(tetrahydropyran-2-ylmethyl)-[1,2,4]triazolo[4,3-a]pyrazin-8-one; Isomer 2

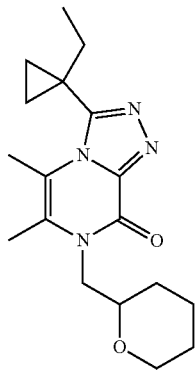 [SMILES: CCC1(c2nnc3c(=O)n(CC4CCCCO4)c(C)c(C)n23)CC1]

Racemic 3-(1-ethylcyclopropyl)-5,6-dimethyl-7-(tetrahydropyran-2-ylmethyl)-[1,2,4]triazolo[4,3-a]pyrazin-8-one (564 mg, 1.71 mmol) is separated into its constituent enantiomers by chiral SFC using the following conditions: Column (S,S) Whelk-01 25 cm×21.2 mm, 10µ, mobile phase 40% EtOH 75% $CO_2$, flow rate 5 mL/minute, UV 225 nm, column temperature 35° C. The first eluting material is isolated as the title compound of Example 11 (262 mg, 46.5%), MS (m/z) 331 (M+H), $t_{(R)}$=1.99 minutes, ee >99%. The second eluting material is isolated as the title compound of Example 12 (248 mg, 44%). MS (m/z) 331 (M+H), $t_{(R)}$=3.03 minutes, ee >99%.

Example 13

5,6-Dimethyl-3-(1-methylcyclopropyl)-7-(tetrahydropyran-2-ylmethyl)-[1,2,4]triazolo[4,3-a]pyrazin-8-one; Isomer 1 and

Example 14

5,6-Dimethyl-3-(1-methylcyclopropyl)-7-(tetrahydropyran-2-ylmethyl)-[1,2,4]triazolo[4,3-a]pyrazin-8-one; Isomer 2

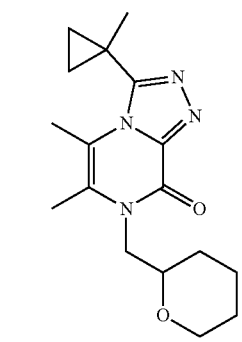 [SMILES: Cc1c(C)n2c(C3(C)CC3)nnc2c(=O)n1CC1CCCCO1]

Racemic 5,6-dimethyl-3-(1-methylcyclopropyl)-7-(tetrahydropyran-2-ylmethyl)-[1,2,4]triazolo[4,3-a]pyrazin-8-one (210 mg, 0.664 mmol) is separated into its constituent enantiomers by chiral SFC using the following conditions: Column (S,S) Whelk-01 25 cm×21.2 mm, 10µ, mobile phase 35% EtOH/$CO_2$, flow rate 5 mL/minute, UV 225 nm, column temperature 40° C. The first eluting material is isolated to give the title compound of Example 13 (60 mg, 28.6%), MS (m/z) 317 (M+H), $t_{(R)}$=1.84 minutes, ee >99%. The second eluting material is isolated to give the title compound of Example 14 (55 mg, 26.2%), MS (m/z) 317 (M+H), $t_{(R)}$=2.65 minutes, ee >99%.

Example 15

3-(1-Cyclopropylcyclopropyl)-5,6-dimethyl-7-[(1-methylcyclopropyl)methyl]-[1,2,4]triazolo[4,3-a]pyrazin-8-one

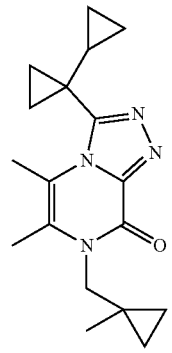 [SMILES: Cc1c(C)n2c(C3(C4CC4)CC3)nnc2c(=O)n1CC1(C)CC1]

Scheme 3, step 4: 3-(1-Cyclopropylcyclopropyl)-5,6-dimethyl-7H-[1,2,4]triazolo[4,3-a]pyrazin-8-one (350 mg, 1.43 mmol), cesium carbonate (1.40 g, 4.3 mmol), and (1-methylcyclopropyl)methyl methanesulfonate (250 mg, 1.52 mmol) are combined in DMSO (7 mL). The mixture is stirred under $N_2$ at room temperature overnight. The reaction is diluted with EtOAc and washed with brine. The aqueous layer is extracted with EtOAc and the combined organics are dried over anhydrous sodium sulfate, filtered, and concentrated under reduced pressure. The residue is purified by reverse phase flash chromatography on C18, eluting with 10-60% ACN in $H_2O$ and lyophilized to give the title compound (2 mg, 0.45%). MS (m/z) 313 (M+H).

Example 16

7-Butyl-3-(1-cyclopropylcyclopropyl)-5-ethyl-6-methyl-[1,2,4]triazolo[4,3-a]pyrazin-8-one

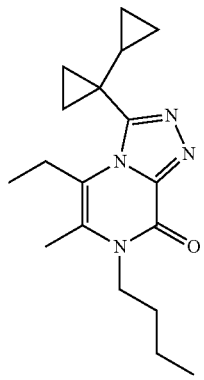 [SMILES: CCCCn1c(C)c(CC)n2c(C3(C4CC4)CC3)nnc2c1=O]

Scheme 2, step 6: N'-(4-Butyl-6-ethyl-5-methyl-3-oxo-pyrazin-2-yl)-1-cyclopropyl-cyclopropanecarbohydrazide (576.1 mg, 1.213 mmol, 70 mass %) in hexamethyldisilazane (4 mL) is stirred at 120° C. overnight. The reaction mixture is cooled to room temperature, poured into MeOH. Upon addition to MeOH, the reaction mixture violently erupted. The resulting residue is purified by silica gel flash chromatography eluting with 0-10% MeOH in DCM. The resulting residue is dissolved in hexamethyldisilazane (4 mL) and is stirred at 120° C. overnight. The reaction mixture is cooled to room temperature, MeOH is added, the reaction is stirred at 50° C. for 30 minutes and concentrated under reduced pressure. The residue is purified by silica gel flash chromatography eluting with 0-10% MeOH in DCM. The material is further purified by reverse phase flash chromatography on C18, eluting in 10-100% ACN in $H_2O$ (0.1% ammonium bicarbonate) to give the title compound (101.7 mg, 27%). MS (m/z) 315 (M+H).

Generation of PDE Proteins

The nucleotide sequences encoding full-length human PDE1A (NP_001003683.1) and PDE1C (NP_005011.1) are inserted into pFastBac1 (Invitrogen) vector with an N-terminal HIS tag. The nucleotide sequences encoding full-length human PDE4D (NP_006194.2) and catalytic domain (residue 641-1141) of PDE3A (NP_000912.3) are inserted into pFastBac1 (Invitrogen) vector with a C-terminal HIS tag. The nucleotide sequences encoding full-length human PDE6A (NP_000431.2) and PDE6B (AAH00249.1) are inserted into pFastBacDual (Invitrogen) vector with an N-terminal HIS tag and N-terminal Flag tag, respectively, for production of PDE6A/6B dimer. Baculovirus generation and protein expression in Sf9 cells are carried out according to the protocol of Bac-to-Bac Baculovirus Expression system (Invitrogen). The nucleotide sequence encoding full-length human PDE1B (NP_000915.1) is inserted into pIEX4 (Novagen) with a C-terminal HIS tag, and both protein productions in Sf9 cells are carried out according to the vendor's protocol (Novagen). The His tagged PDE proteins are purified using Ni-NTA agarose (Qiagen) followed by size exclusion chromatography on a SUPERDEX© 200 column (GE Healthcare) in storage buffer (20 mM Tris-HCl, pH 7.5, 150 mM NaCl, 10% Glycerol). The Flag tagged PDE proteins including PDE6A/6B are purified using anti-Flag M2-agarose (Sigma), after purification through NiNTA column chromatography and eluted in storage buffer (50 mM Tris-HCl, pH 7.5, 150 mM NaCl, 10% Glycerol, 0.1 mg/ml Flag peptide). All purified proteins are stored at −80° C. in small aliquots.

Phosphodiesterase Enzyme Assays

All 3', 5' cyclic nucleotide PDE enzyme activities are measured with a radiometric enzyme assay based on SPA detection system. Compounds to be tested are diluted in pure DMSO using ten point concentration response curves. Maximal compound concentration in the reaction mixture is either 10 or 100 µM. Compounds at the appropriate concentration are pre-incubated with either of the PDE enzymes for 30 minutes before the reaction is started by the addition of substrate. Reactions are allowed to proceed for 60 minutes at room temperature. Next, reactions are stopped by addition of SPA beads. Samples are read 12 hours later in a MICROBETA™ TRILUX© Counter. $IC_{50}$ values are calculated by plotting the normalized data vs. log [compound] and fitting the data using a four parameter logistic equation.

$Ca^{2+}$-Calmodulin Dependent PDE Enzyme Assays

PDE1B, PDE1A, and PDE1C are cloned and purified following standard protein generation procedures. The assay buffer is prepared to give a final concentration in the assay of 50 mM Tris-HCl, 50 mM MgCl2, 4 mM $CaCl_2$), 0.1% BSA and 6 U/mL Calmodulin in water, at pH 7.5. The final enzyme concentration is 0.25, 0.074 and 0.0012 nM, for PDE1A, PDE1B and PDE1C respectively. The reactions are started by addition of the substrate, [$^3$H]cAMP, to give a final concentration of 47 nM.

In Vitro Potency of Examples Compounds Against Human PDE1A, PDE1B, and PDE1C

TABLE 5

| Example | PDE 1A $IC_{50}$ (nM) | PDE 1B $IC_{50}$ (nM) | PDE 1C $IC_{50}$ (nM) |
|---|---|---|---|
| 1 | 20.3 ± 0.5, n = 2 | 29.4 ± 11.6, n = 2 | 12 ± 4, n = 2 |
| 2 | 3.73 ± 2.02, n = 7 | 4.11 ± 1.10, n = 6 | 2.81 ± 0.88, n = 6 |

TABLE 5-continued

| Example | PDE 1A IC$_{50}$ (nM) | PDE 1B IC$_{50}$ (nM) | PDE 1C IC$_{50}$ (nM) |
| --- | --- | --- | --- |
| 3 | 11 ± 2, n = 3 | 9.36 ± 2.01, n = 2 | 1.26 ± 0.61, n = 2 |
| 4 | 3.71 ± 0.08, n = 2 | 3.65 ± 1.88, n = 2 | 1.06 ± 0.24, n = 2 |
| 5 | 11.5 ± 3.6, n = 2 | 11.1 ± 3.0, n = 2 | 2.70 ± 0.16, n = 2 |
| 6 | 5.98 ± 0.49, n = 3 | 7.03 ± 4.13, n = 3 | 1.88 ± 0.56, n = 3 |
| 7 | 32.7 | 28.51 | 7.76 |
| 8 | 25.39 ± 3.08, n = 2 | 36.9 ± 9.8, n = 2 | 10.1 ± 2.3, n = 2 |
| 9 | 3.73 ± 0.26, n = 2 | 4.94 ± 0.57, n = 2 | 0.958 ± 0.487, n = 2 |
| 10 | 6.72 ± 2.03, n = 2 | 10.6 ± 2.0, n = 2 | 2.00 ± 0.311, n = 2 |
| 11 | 13.16 | 17.6 ± 5.2, n = 2 | 4.77 ± 0.06, n = 2 |
| 12 | 44.64 | 33.88 | 13.16 |
| 13 | 21.8 ± 3.0, n = 2 | 21.8 ± 3.0, n = 2 | 6.35 ± 2.34, n = 2 |
| 14 | 52.35 | 48.02 | 22.33 |
| 15 | 3.1 ± 1.1, n = 7 | 4.9 ± 1.8, n = 7 | 1.4 ± 0.3, n = 7 |
| 16 | 8.67 ± 7.91, n = 2 | 6.54 ± 2.61, n = 2 | 1.20 ± 0.94, n = 2 |

Mean ± standard deviation

The data in Table 5 demonstrate that the compounds of Examples 1-16 inhibit human PDE1A, PDE1B, and PDE1C enzyme activity in vitro.

PDE Enzyme Assays Using [3H]cAMP as Substrate

The following PDE activities are measured using [3H] cAMP as reaction substrate: human PDE3A (catalytic domain) and human PDE4D. Both enzymes are cloned and purified following standard procedures. The assay buffer is prepared to give a final concentration in the assay of 50 mM Tris-HCl, 8.3 mM MgCl2, 1.7 mM EDTA and 0.1% BSA at pH 7.5. Final enzyme concentrations are 0.008 and 0.021 nM for PDE3A and PDE4D, respectively. Reactions are started by addition of the substrate, [3H]cAMP, to give a final concentration of 47 nM.

In Vitro Potency of Examples Compounds Against Human PDE3A (Catalytic Domain) and PDE4D

TABLE 6

| Example | PDE3A IC$_{50}$ (μM) | PDE4D IC$_{50}$ (μM) |
| --- | --- | --- |
| 1 | >100.0 | 5.59 |
| 2 | >100.0 | 23.8 ± 0.8, n = 2 |
| 3 | >100.0 | 14.33 |
| 4 | >100.0 | 23.99 |
| 5 | >100.0 | 29.88 |
| 6 | >100.0 | 30.86 |
| 7 | >100.0 | 46.5 |
| 8 | >100.0 | 57.67 |
| 9 | >100.0 | 33.1 |
| 10 | >100.0 | 21.39 |
| 11 | >100.0 | 67.2 |
| 12 | >100.0 | 30.99 |
| 13 | >100.0 | >100.0 |
| 14 | >100.0 | 40.78 |
| 15 | 9.600 | 14.0 ± 1.3, n = 4 |
| 16 | >100.0 | 22.3 |

Mean ± standard deviation

PDE Enzyme Assays Using [3H]cGMP as Substrate

The following phosphodiesterase activities are measured using [3H]cGMP as reaction substrate: human PDE6A/6B. The catalytic active form of human PDE6 is a dimer composed of an a (human PDE6A) and β subunits (human PDE6B). The dimer of human PDE6A/6B is produced by the coexpression and purification strategy, using two purification steps, i.e., NiNTA and anti-FLAG Sepharose chromatography. The assay buffer is prepared to give a final concentration in the assay of 50 mM Tris-HCl, 8.3 mM MgCl2, 1.7 mM EDTA and 0.1% BSA at pH 7.5. The final enzyme concentration is 5 nM. The reactions are started by addition of the substrate, [3H]cGMP, to give a final concentration of 80 nM.

In Vitro Potency of Example Compounds Against PDE6AB

TABLE 7

| Example | PDE6AB IC$_{50}$ (μM) |
| --- | --- |
| 1 | >10.00 |
| 2 | >10.00 |
| 3 | >10.00 |
| 4 | >10.00 |
| 5 | >10.00 |
| 6 | >10.00 |
| 7 | >10.00 |
| 8 | 2.659 |
| 9 | >10.00 |
| 10 | >10.00 |
| 11 | >10.00 |
| 12 | 7.623 |
| 13 | >10.00 |
| 14 | >10.00 |
| 15 | >10.00 |
| 16 | >10.00 |

The data in Tables 5, 6, and 7 demonstrate that the compounds of Examples 1-16 are selective inhibitors of human PDE1A, PDE1B, and PDE1C relative to human PDE3A, PDE4D, and PDE6AB in vitro.

We claim:
1. A compound of formula I:

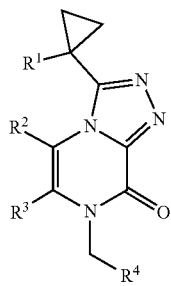

or a pharmaceutically acceptable salt or stereoisomer thereof,
wherein:
R$^1$ is CH$_3$, CH$_2$CH$_3$, or cyclopropyl;
R$^2$ is H, CH$_3$, or CH$_2$CH$_3$;
R$^3$ is CH$_3$ or CH$_2$-(1-methylpyrazol-4-yl); and
R$^4$ is C$_2$-C$_4$ alkyl, 1-methylcyclopropyl, or tetrahydropyran-2-yl.

2. The compound according to claim 1, or a pharmaceutically acceptable salt or stereoisomer thereof, wherein R$^1$ is cyclopropyl.

3. The compound according to claim 1, or a pharmaceutically acceptable salt or stereoisomer thereof, wherein R$^2$ is CH$_3$.

4. The compound according to claim 1, or a pharmaceutically acceptable salt or stereoisomer thereof, wherein R$^3$ is CH$_3$.

5. The compound according to claim 1, wherein the compound is:

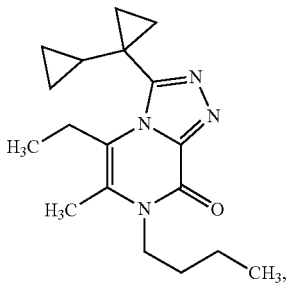 [SMILES: CCCCn1c(C)c(CC)n2c(C3(C4CC4)CC3)nnc2c1=O]

or a pharmaceutically acceptable salt thereof.

6. The compound according to claim 1, wherein the compound is:

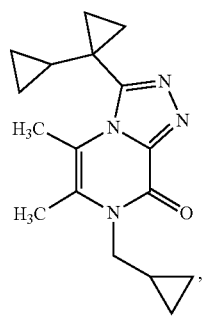 [SMILES: Cc1c(C)n2c(C3(C4CC4)CC3)nnc2c(=O)n1CC1CC1]

or a pharmaceutically acceptable salt thereof.

7. The compound according to claim 1, wherein the compound is:

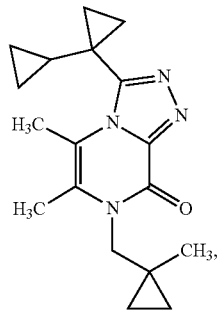 [SMILES: Cc1c(C)n2c(C3(C4CC4)CC3)nnc2c(=O)n1CC1(C)CC1]

or a pharmaceutically acceptable salt thereof.

8. The compound according to claim 1, wherein the compound is:

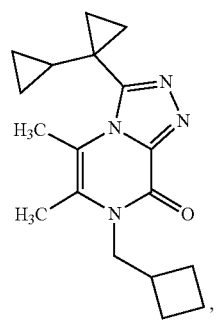 [SMILES: Cc1c(C)n2c(C3(C4CC4)CC3)nnc2c(=O)n1CC1CCC1]

or a pharmaceutically acceptable salt thereof.

9. A pharmaceutical composition comprising at least one pharmaceutically acceptable carrier, diluent, or excipient and a compound according to claim 1, or a pharmaceutically acceptable salt or stereoisomer thereof.

10. A method for treating chronic kidney disease in a patient, wherein the method comprises administering to the patient in need thereof a therapeutically effective amount of a compound according to claim 1, or a pharmaceutically acceptable salt or stereoisomer thereof.

11. A method for treating diabetic kidney disease in a patient, wherein the method comprises administering to the patient in need thereof a therapeutically effective amount of a compound according to claim 1, or a pharmaceutically acceptable salt or stereoisomer thereof.

12. A process for preparing the pharmaceutical composition according to claim 9, wherein the process comprises admixing at least one pharmaceutically acceptable carrier, diluent, or excipient with a compound according to claim 1, or a pharmaceutically acceptable salt or stereoisomer thereof.

* * * * *